United States Patent
Fountains, III et al.

(10) Patent No.: US 6,796,166 B1
(45) Date of Patent: Sep. 28, 2004

(54) ALL POLYMER HUMIDITY SENSOR BASED ON LASER CARBONIZED POLYIMIDE SUBSTRATE

(75) Inventors: Augustus Way Fountains, III, West Point, NY (US); John M. Ingram, Fort Leavenworth, KS (US); James A. Nicholson, Clarksville, TN (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 53 days.

(21) Appl. No.: 10/307,458

(22) Filed: Dec. 2, 2002

(51) Int. Cl.$^7$ .............................................. G01N 19/10
(52) U.S. Cl. .................... 73/29.05; 73/335.04; 73/29.01
(58) Field of Search .......................... 73/29.01, 335.03, 73/335.04, 29.05

(56) References Cited

U.S. PATENT DOCUMENTS

| | | | |
|---|---|---|---|
| 4,529,642 A | 7/1985 | Miyoshi et al. | |
| 4,572,843 A | * 2/1986 | Saito et al. | ................... 427/554 |
| 5,075,667 A | 12/1991 | Nishiwaki et al. | |
| 5,608,374 A | 3/1997 | Ikejiri | |
| 6,071,597 A | 6/2000 | Yang et al. | |
| 6,247,349 B1 | 6/2001 | Lee et al. | ................... 73/29.05 |
| 6,299,850 B1 | * 10/2001 | Doughty et al. | ........ 423/445 R |
| 6,399,669 B1 | * 6/2002 | Suzuki et al. | ................ 521/183 |
| 6,501,640 B1 | * 12/2002 | Niiori et al. | ................. 361/504 |

* cited by examiner

Primary Examiner—Daniel S. Larkin
(74) Attorney, Agent, or Firm—William V. Adams

(57) ABSTRACT

A sensing device formed upon a substrate, including a method of forming the sensing device. A substrate can be provided, which is formed from a polymer. A sensor circuit can then be patterned and formed upon the substrate. One or more carbonized filaments can also be formed upon the substrate for use with the sensor circuit. The sensor circuit itself can comprise a capacitive type sensor circuit. A polymer can be coated over the sensor circuit and circuit components thereof to form an all polymer sensor for use in detecting chemical agents. Such a hygrosensitive polymer can comprise, for example, HMPTAC (2-hydroxy-3-methacryloxypropyl trimethylammonium chloride). The all polymer sensor formed thereof can also be utilized as a humidity sensor. The polymer can be laser carbonized by an argon ion laser to form the plurality of carbonized filaments.

20 Claims, 2 Drawing Sheets

ALL POLYMER HUMIDITY SENSOR BASED ON LASER CARBONIZED POLYIMIDE SUBSTRATE

STATEMENT OF GOVERNMENT INTEREST

The invention described herein may be manufactured and used by or for the United States Government for Governmental purposes without the payment of any royalties.

TECHNICAL FIELD

The present invention generally relates to sensor methods and systems. The present invention specifically relates to sensor methods and systems for detecting chemical agents and gases. The present invention also relates to humidity sensors. Additionally, the present invention relates to polymer humidity sensors and sensor substrates thereof.

BACKGROUND OF THE INVENTION

A variety of sensors for detecting chemical agents and gases have been developed. A basic chemical detecting sensor well known in the art is a humidity sensor. In general, a humidity sensor measures the humidity level by measuring the change in the resistance of an element or the change in the electrostatic capacity of that element as it absorbs or releases moisture. Such sensors can also be utilized for detecting chemicals and gases, in addition to merely the level humidity available in a given environment Generally, humidity sensors can be classified as belonging to either one of two classes—a resistance type (or resistance-variation type) humidity sensor and a capacitance type (or capacitance-variation type) humidity sensor. A resistance type humidity sensor detects relative humidity by measuring the change in the resistance of an element corresponding to the ambient humidity. In comparison, a capacitance type humidity sensor detects humidity by measuring the change in the electrostatic capacity of an element corresponding to the ambient humidity. The capacitance type humidity sensors typically do not exhibit a satisfactory linear relationship between the capacitance and humidity, and an external circuit is required to overcome this disadvantage. This increases the manufacturing cost of capacitance-change type humidity sensors. Thus, the resistance type humidity sensors, which generally exhibit a linear relationship between the resistance and humidity, appear to have been the preferred choice.

Most of the resistance type humidity sensors include an electrolytic, polymeric, or metallic oxide sensor element. An electrolytic sensor element, which has become the most predominant type of humidity sensors, can be constructed by forming a layer of moisture-lyzable (i.e., hydrolyzed by moisture) electrolyte on an insulating moisture-absorbing substrate. Polymeric films have been used as a humidity-sensing element. Polymer-based humidity-sensing elements can generally be classified into two categories: capacitance-type and impedance-type. The former typically involves more complicated circuit design and manufacturing process, and thus is more expensive, than the latter. An impedance-type electric humidity-sensing element changes its electrical impedance as the humidity of the surrounding environment changes, and the measured impedance is converted into humidity readings. The polymer-based sensing elements can also be further classified into two categories: porous (or more specifically, micro-porous) type, and non-porous type.

The problem of developing small, real time point detection systems for chemical agents is being addressed by laboratories and research facilities in the United States and throughout the world. These laboratories and research facilities have attacked the problem by developing various detection schemes, but virtually all utilize the same substrate to build their sensing device: a silicon or alumina platform with deposited gold or platinum wiring. This substrate introduces special problems to the sensor design. Silica substrates with gold wiring are expensive and sometimes need to be post-processed at the manufacturing facility. Both silica and alumina substrates have shown polymer adhesion problems, which presents difficulties in polymer based humidity sensors, particularly those adapted for use in detecting chemical agents. Alumina is also a relatively good thermal conductor, which can lead to sensor film breakdown. Silica is brittle and alumina is rigid. While cost issues and fabrication problems can be overcome in a laboratory or research environment, this is not true in current commercial manufacturing facilities.

Based on the foregoing, the present inventors have concluded that an alternative substrate for a sensing device must be developed in order to increase the efficiency and deployment of sensing devices used to detect chemical agents and gases, including humidity-types sensors. A stable and reliable substrate foundation is an important factor in sensor efficiency. Important factors in implementing a sensor include the accuracy, interchangeability, long-term stability, resistance to chemical and physical contaminants, along with size and cost effectiveness. Such factors can be addressed through the development of an improved sensor substrate. The present inventors have conducted research and experiments aimed at addressing this substrate issue. As a result of this research and experimentation, the present inventors believe that a polymer presents a good candidate for an ideal sensor substrate. The use of a polymer as a sensor substrate is described in greater detail herein.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide improved sensor methods and systems.

It is yet another aspect of the present invention to provide an improved sensor for detecting chemical agents and gases.

It is also an aspect of the present invention to provide an improved humidity sensor.

It is yet another aspect of the present invention to provide an improved substrate upon which sensors for detecting chemical agents and gases can be formed.

It is still another aspect of the present invention to provide a polymer as an ideal sensor substrate.

The above and other aspects can be achieved as is now described. A sensing device formed upon a substrate, including a method of forming the sensing device, is disclosed herein. A substrate can be provided, which is formed from a polymer. A sensor circuit can then be patterned and formed upon the substrate. One or more carbonized filaments can also be formed upon the substrate for use with the sensor circuit. The sensor circuit itself can comprise a capacitive type sensor circuit. A polymer can be coated over the sensor circuit and circuit components thereof to form an all polymer sensor for use in detecting chemical agents. Such a polymer can comprise, for example, HMPTAC (2-hydroxy- 3-methacryloxypropyl trimethylammonium chloride). The all polymer sensor formed thereof can also be utilized as a humidity sensor. The polymer can be laser carbonized by an argon ion laser to form the plurality of carbonized filaments. The polymer itself can comprise KAPTON®.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and, together with the detailed description of the invention, serve to explain the principles of the present invention.

DETAILED DESCRIPTION OF THE INVENTION

The particular values and configurations discussed in these non-limiting examples can be: varied and are cited merely to illustrate embodiments of the present invention and are not intended to limit the scope of the invention.

Figure 1:
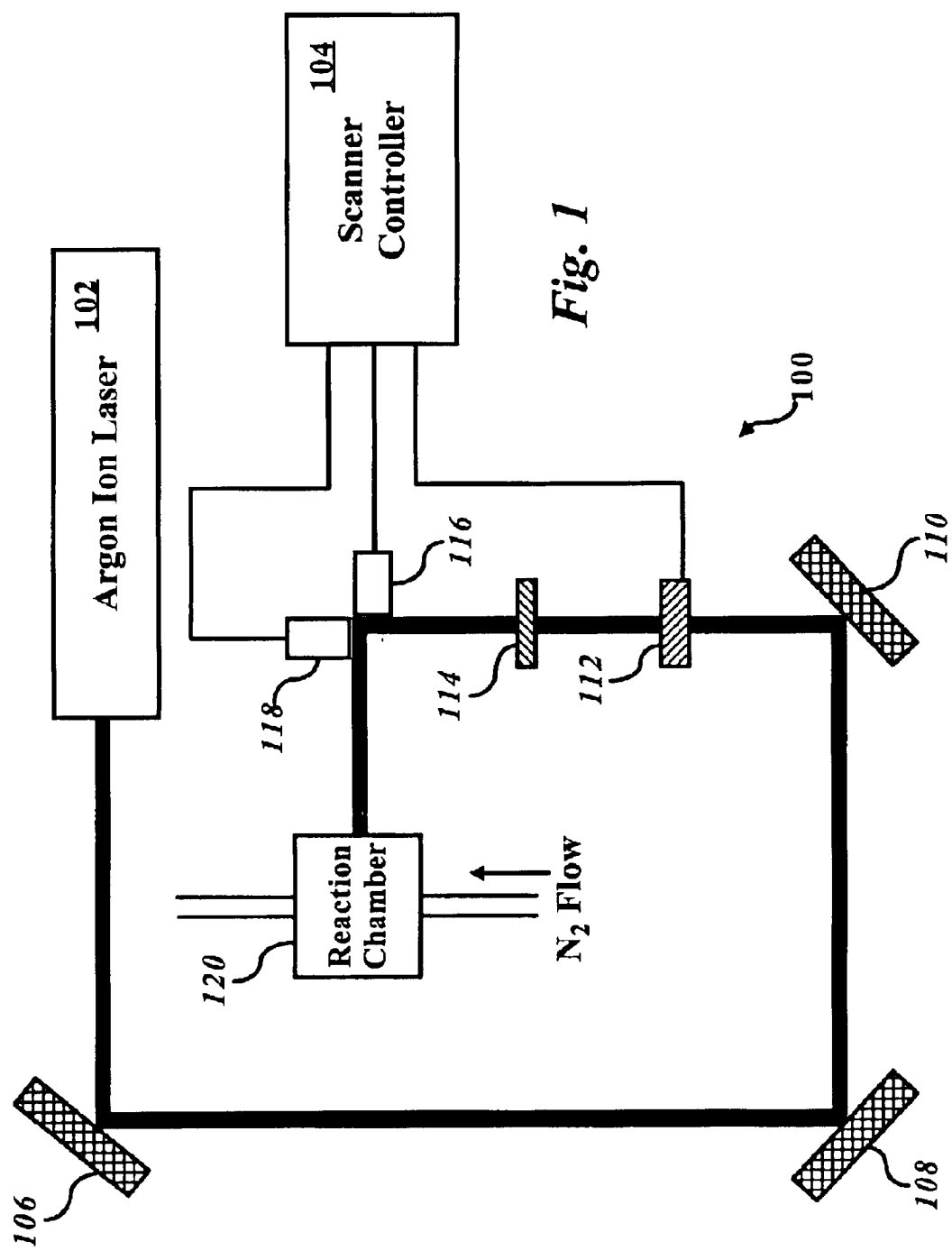
FIG. 1 illustrates a schematic diagram illustrating a design for the laser pyrolysis of a polymer for use as a sensor substrate, in accordance with a preferred embodiment of the present invention.

FIG. 1 illustrates a schematic diagram 100 illustrating a design for the laser pyrolysis of a polymer for use as a sensor substrate, in accordance with a preferred embodiment of the present invention. As illustrated in diagram 100, an argon ion laser 102 can be utilized to pyrolyze a polymer located in a reaction chamber 120. The polymer located within reaction chamber 120 generally comprises a sensor substrate upon which a sensor circuit can be patterned and formed. Argon ion laser 102 can comprise, for example, a COHERENT® Innova 200 argon ion laser operating at 514 nm and can deliver an argon laser beam to reaction chamber 120 along a path from argon laser 102 to a first mirror 106, a second mirror 108, a third mirror 110, a mechanical aperture 112, a lens 114, first and second servo mirrors 116 and 118, and finally to reaction chamber 120. Note that COHERENT® is a registered trademark of Coherent, Inc., a company with headquarters in Santa Clara, Calif. It can be appreciated by those skilled in the art that argon ion laser 102 can comprise other types of argon ion lasers. Thus, the specific use of the COHERENT® Innova 200 argon ion laser is described herein for illustrative and exemplary purposes only and is not considered a limiting feature of the present invention.

Reaction chamber 120 provides nitrogen in an environment in which pyrolysis can take place. Reaction chamber 120 can be configured, for example, as a 10×5×8 cm black aluminum box with a removably sealed lid and a rubber gasket thereof. Reaction chamber 120 can also include a ¼ inch inlet and exhaust port to deliver an argon gas flow at approximately 500 ml/min throughout pyrolysis. One side of reaction chamber 120 may include a 1cm thick quartz window. Those skilled in the art can appreciate, of course, that the aforementioned dimensions and components of reaction chamber 120 can be modified. Such dimensions and measurements are described herein for general edification and background purposes only and do not comprise limiting features of the present invention.

Reaction chamber 120 generally serves two purposes. First, the atmosphere surrounding the polymer contained within reaction chamber 120 can be controlled and hazardous byproducts of pyrolysis thereof can be exhausted safely. The sensor substrate (not shown), which is located within reaction chamber 120 for pyrolization thereof, can be formed from a polymer, such as KAPTON®. For example, 500 HN (127 μm thick) KAPTON® sheets can be utilized as received for use to form a sensor substrate in accordance with the present invention. A sensor pattern can thus be laser carbonized onto a 3×1 cm piece of KAPTON® under an argon atmosphere within reaction chamber 120 (i.e., a pyrolysis chamber). Note that KAPTON® is a registered trademark of E. I. Du Pont De Nemours and Company Corporation, with headquarters in Wilmington, Del., and refers both to a polyimide film for general use in the industrial arts and a flexible film for electrical insulation.

A scanning controller 104 associated with a scanner can be utilized to control the laser pattern on the KAPTON® surface. An example of a scanner, which may be utilized in association with the present invention disclosed herein, is a General Scanning, Inc. DE 2000 scanner. Utilizing a set of computer controlled servo mirrors 116 and 118, an inter-digitated circuit can thus be formed on the surface of the polymer, such as, for example, KAPTON® . Thus, a KAPTON® polyimide film can be utilized as a viable sensor substrate utilizing, for example, a capacitive type humidity sensor design. KAPTON® is one example of a polyimide that can be laser-pyrolized to form conducting filaments of a sensor.

The laser beam provided by argon laser 102 can be focused utilizing lens 114. Such a lens can be, for example, a $CaF_2$ piano convex lens having a focal length of approximately 20 cm. Carbonization of a typical sensor can be carried out with an energy density of 60 to 180 $J/cm^2$. Energy density is a function of scan speed, laser power, total number of scans, and the pyrolysis wavelength. Those skilled in the art can appreciate that this energy density may vary, depending on a desired implementation of the present invention disclosed herein. For example, a filament can be formed with an energy density of 180 $J/cm^2$ at a pyrolysis wavelength of approximately 514 nm. The sensor substrate can thus be optimized for sensitivity by varying the pyrolysis wavelength and energy density.

Figure 2:
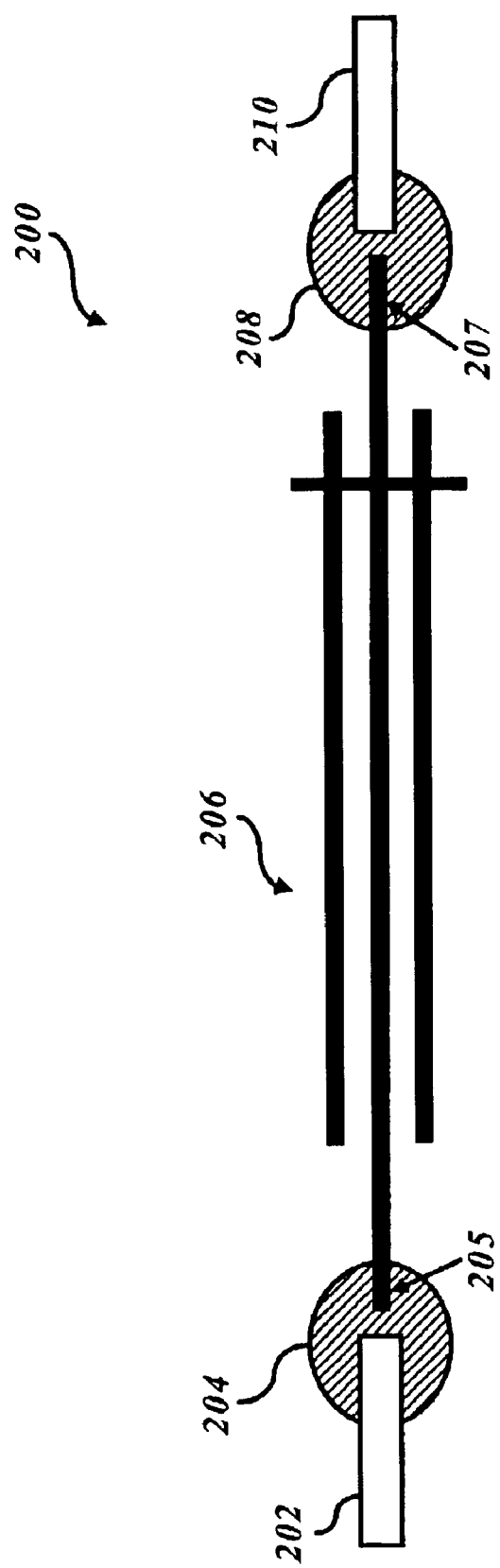
FIG. 2 depicts a diagram of a tongue and fork sensor design in accordance with a preferred embodiment of the present invention.

FIG. 2 depicts a diagram 200 of a tongue and fork sensor design in accordance with a preferred embodiment of the present invention. One or more carbonized filaments 206 can be formed from the sensor substrate, which is located within reaction chamber 120 of FIG. 1 during pyrolization thereof. Carbonized filament 206 can be formed in a tongue and fork configuration, such that one end of 205 of carbonized filament 205 comes into contact with silver paint 204, which in turn comes into contact with the wire end lead 202. Similarly, an end 207 carbonized filament 207 can come into contact with silver paint 208, which in turn can come into contact with wire end lead 210. The approximate diameter of each silver paint area can be, for example, approximately 5 mm. Those skilled in the art can appreciate that although silver paint 204 and 208 are depicted as comprising circular areas, such a circular configuration is presented herein for illustrative purposes only. The silver paint may be arranged as a blotch or other irregular shape.

Thus, the sensor substrate can be taped to a glass slide to provide rigidity throughout fabrication and testing. Wire leads (i.e., with wire end leads 202 and 210) can be respectively attached to ends 205 and 207 of the carbonized filament 206 utilizing silver paint 204 and 208. The substrate thereof can then be drop coated utilizing a polymer coating, such as, for example HMPTAC (2-hydroxy-3- methacryloxypropyl trimethylammonium chloride in the dry nitrogen atmosphere provided by reaction chamber 210 of FIG. 1. Coating of the substrate with such a polymer coating takes place within an inert atmosphere provided by reaction chamber 210. Although a nitrogen atmosphere is discussed generally herein, it can be appreciated by those skilled in the art that an inert atmosphere, such as argon, may be utilized instead of nitrogen, in accordance with the apparatus and method disclosed herein.

The substrate can be drop coated, for example, utilizing a 7.22 mg/mL HMPTAC/methanol solution. The sensor can then be dried at 40° C. for twenty-four hours before testing. A 99.9% anhydrous methanol can be utilized in association with the HMPTAC. Excess solid HMPTAC can be placed in the methanol at room temperature and sonicated for approximately two hours. The saturated solution can be separated from any remaining solid material. Argon laser 102 can be utilized to pyrolyze the polymer substrate to form raised carbonized filaments thereof (i.e., a plurality of carbonized filaments) associated with the sensor circuit formed and patterned on the sensor substrate. The sensor circuit can be coated with a polymer, such as, for example HMPTAC (2-hydroxy-3-methacryloxypropyl trimethylammonium chloride), to form an all polymer sensor thereof.

Impedance measurements of the resulting all polymer sensor can show a continuous response over 5–95% relative humidity. The sensor can be optimized for dynamic range by varying the filament conductivity, sensor area, and HMPTAC thickness. The sensor can also be tested for voltage, temperature, and frequency dependence. An optimized sensor design can be compared to a sensor formed on an alumina/gold substrate. Additionally, by varying the surface pyrolysis energy density, filaments of different size and conductivity can be constructed. Initial experiments by the present inventors have indicated that filament conductivity size can have a small effect on sensor performance.

The sensor area comprises the amount of polymeric surface that interacts with the analyte gas between the carbonized filaments. The different combinations of circuit design and filament spacing can manipulate the sensor area A basic sensor design can be based on a capacitive type circuit with impedance being the measured circuit parameter. Several circuit designs can thus be configured ranging from the tongue and fork design illustrated in FIG. 2 to a six-fingered comb design. Filament spacing is defined as the distance measured between two filaments. The filament spacing can be viewed as the dielectric distance between two capacitive plates. By varying the design configuration and the filament spacing, the area between filaments can be optimized for the widest dynamic range.

A greater dynamic range can be shown to correlate with a smaller interaction area. The widest sensor range has been found utilizing a simple tongue and fork design, such as that illustrated in FIG. 2, with a 20 $\mu$m-filament spacing. The sensor's behavior appears intuitive. It thus follows that the less sensor area: the greater the sensitivity to a change in the environment, the wider the sensor's response. The thickness of the HMPTAC sensing material is directly related to the sensitivity of the sensor and its response time. Thus, the HMPTAC thickness can be defined as the amount of HMPTAC polymer drop coated onto the sensor area.

The present invention offers several advantages over the prior art. An all polymer sensor substrate, as indicated herein, can be a viable solution for the alumina/gold substrates utilized in current sensor designs. The dynamic sensing range, response time and hysteresis is comparable to the alumina/gold sensor substrate. Small differences in performance can be attributed to sensor design rather than substrate characteristics. The present invention can also be adapted for use in producing chemical sensor devices other than simply humidity sensors.

The present invention disclosed herein thus generally comprises a sensing device formed upon a substrate, including a method of forming the sensing device, are disclosed herein. A substrate can be provided, which is formed from a polymer. A sensor circuit can then be patterned and formed upon the substrate. One or more carbonized filaments can also be formed upon the substrate for use with the sensor circuit. The sensor circuit itself can comprise a capacitive type sensor circuit. Additionally, a polymer can be coated over the sensor circuit and circuit components thereof to form an all polymer sensor for use in detecting chemical agents. Such a polymer may comprise a hygrosensitive polymer. HMPTAC (2-hydroxy-3-methacryloxypropyl trimethylammonium chloride), for example, can be coated over the sensor circuit and associated circuit components. Coating of the sensor substrate by a polymer coating, including the sensor circuit and components thereof can take place within an inert atmosphere, such as an argon or nitrogen atmosphere. The all polymer sensor formed thereof can also be utilized as a humidity sensor. The polymer can be laser carbonized by an argon ion laser to form the plurality of carbonized filaments. The polymer itself can comprise KAPTON®.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and It is the intent of the appended claims that such variations and modifications be covered. The description as set forth is not intended to be exhaustive or to limit the scope of the invention. Many modifications and variations are possible in light of the above teaching without departing from the scope of the following claims. It is contemplated that the use of the present invention can involve components having different characteristics. It is also intended that the scope of the present invention be defined by the claim appended hereto, giving full cognizance to equivalents in all respects.

What is claimed is:

1. A sensing device formed upon a substrate, said sensing device comprising:

a substrate comprising a polymer upon which a sensor circuit is patterned and formed;

a sensor circuit patterned and formed from said substrate, wherein said sensor circuit comprises at least one carbonized filament formed from said polymer upon said substrate for use with said sensor circuit; and a polymer coating deposited over said sensor circuit and circuit components thereof to thereby form an all polymer sensor for use in detecting chemical agents.

2. The sensing device of claim 1 wherein said polymer is laser carbonized to form said at least one carbonized filament.

3. The sensing device of claim 1 wherein said polymer comprises a polyimide film.

4. The sensing device of claim 1 wherein said polymer comprises an insulator.

5. The sensing device of claim 1 wherein said sensor circuit formed upon said substrate is coated with said polymer coating within an inert atmosphere.

6. The sensing device of claim 5 wherein a reaction chamber provides said nitrogen atmosphere.

7. The sensing device of claim 5 wherein said polymer coating comprises HMPTAC (2-hydroxy-3-methacryloxypropyl trimethylammonium chloride).

8. The sensing device of claim 1 wherein said sensor circuit comprises a capacitive type sensor circuit.

9. The sensing device of claim 7 wherein said polymer sensor comprises a humidity sensor.

10. A humidity sensor formed upon a substrate, said sensing device comprising:

a substrate comprising a polymer upon which a humidity sensor circuit is patterned and formed, wherein said polymer is laser carbonized to form at least one carbonized filament;

a humidity sensor circuit patterned and formed from said substrate, wherein said sensor circuit comprises a capacitive type sensor circuit that includes said at least one carbonized filament formed from said polymer upon said substrate for use with said humidity sensor circuit; and a polymer coating deposited over said humidity sensor circuit and circuit components thereof to thereby form an all polymer humidity sensor for use in detecting humidity of an environment, wherein said substrate is coated with said polymer coating within an inert atmosphere provided by a reaction chamber.

11. A method of forming a sensing device formed upon a substrate, said method comprising the steps of:

providing a substrate comprising a polymer upon which a sensor circuit is patterned and formed;

patterning and forming a sensor circuit from said substrate;

forming at least one carbonized, filament upon said substrate, wherein said at least one carbonized filament is associated with said sensor circuit; and coating said sensor circuit and associated circuit components thereof with a polymer coating to thereby form an all polymer sensor for use in detecting chemical agents.

12. The method device of claim 11 wherein said polymer is laser carbonized to form said at least one carbonized filament.

13. The method device of claim 11 wherein said polymer comprises a polyimide film.

14. The method of claim 11 wherein said polymer comprises an insulator.

15. The method of claim 11 further comprising the step of:

coating said sensor circuit formed upon said substrate with said polymer coating within an inert atmosphere.

16. The method of claim 15 further comprising the step of:

providing said nitrogen atmosphere within a reaction chamber.

17. The method of claim 15 wherein said polymer coating comprises HMPTAC (2-hydroxy-3-methacryloxypropyl trimethylammonium chloride).

18. The method of claim 11 wherein said sensor circuit comprises a capacitive type sensor circuit.

19. The method of claim 18 wherein said polymer sensor comprises a humidity sensor.

20. The method of forming a humidity sensor upon a substrate, said method comprising the steps of:

providing a substrate comprising a polymer upon which a humidity sensor circuit is patterned and formed;

laser carbonizing said polymer to form at least one carbonized filament associated with said humidity sensor circuit;

configuring said humidity sensor circuit as a capacitive type sensor circuit; and coating a said humidity sensor circuit with a polymer coating comprising HMPTAC (2-hydroxy-3-methacryloxypropyl trimethylammonium chloride) within an inert atmosphere provided by a reaction chamber to form an all polymer humidity sensor thereof.

* * * * *